United States Patent [19]

Bartfay-Szabo

[11] 4,188,116
[45] Feb. 12, 1980

[54] ABBE REFRACTOMETER

[75] Inventor: Stephen A. Bartfay-Szabo, Williamsville, N.Y.

[73] Assignee: American Optical Corporation, Southbridge, Mass.

[21] Appl. No.: 879,315

[22] Filed: Feb. 21, 1978

[51] Int. Cl.² .......................................... G01N 21/46
[52] U.S. Cl. ................................. 356/137; 350/285
[58] Field of Search ............... 356/128, 131, 132, 137; 33/1 PT, 1 N; 318/626, 628, 675, 676; 364/525, 559, 817; 350/285

[56] References Cited

U.S. PATENT DOCUMENTS

| 2,724,304 | 11/1955 | Crawford | 356/132 |
| 2,747,455 | 5/1956 | Spracklen et al. | 356/132 |
| 3,754,815 | 8/1973 | Sanctuary et al. | 350/285 |

Primary Examiner—John K. Corbin
Assistant Examiner—Bruce Y. Arnold
Attorney, Agent, or Firm—Jeremiah J. Duggan; Alan H. Spencer; Stephen A. Schneeberger

[57] ABSTRACT

A follower mechanism is used to determine the precise location of a moveable mirror in an Abbe Refractometer to provide the necessary information for converting mirror position to index of refraction. The mechanism is particularly suitable for conversion and readout by electronic means.

9 Claims, 8 Drawing Figures

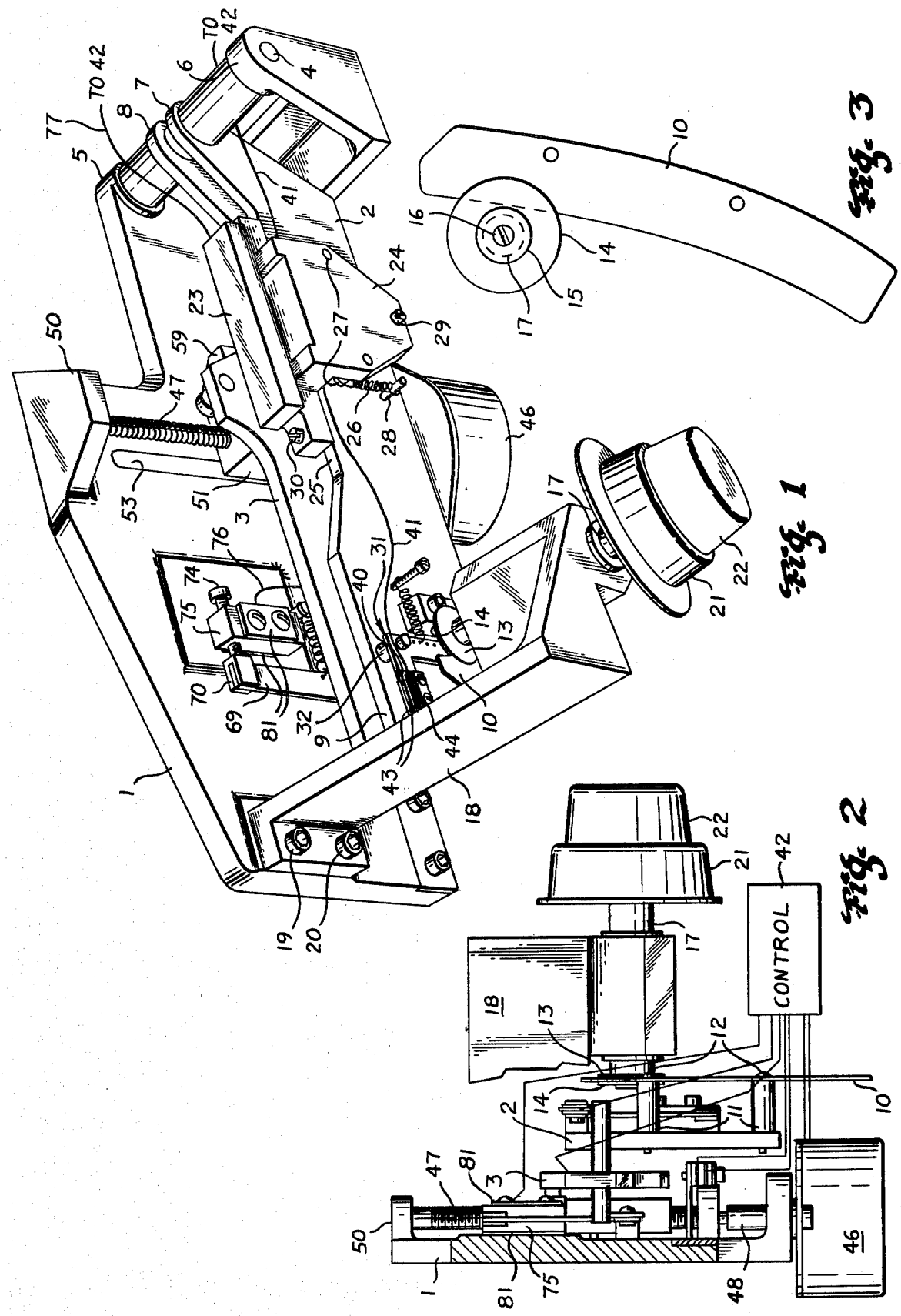

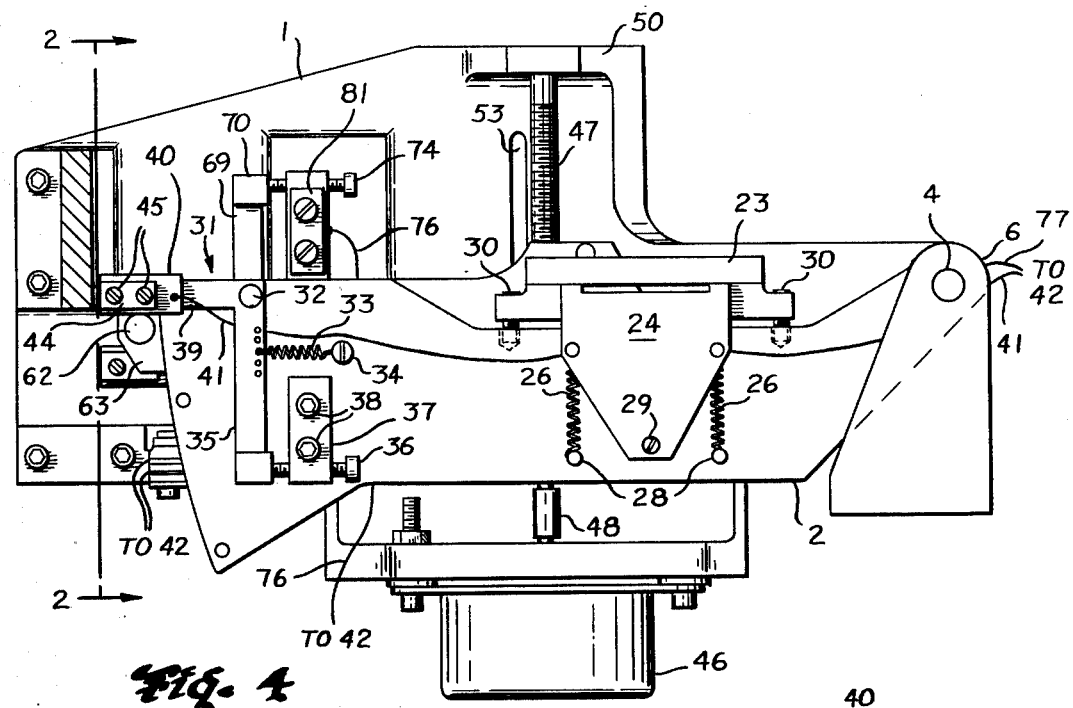
Fig. 4
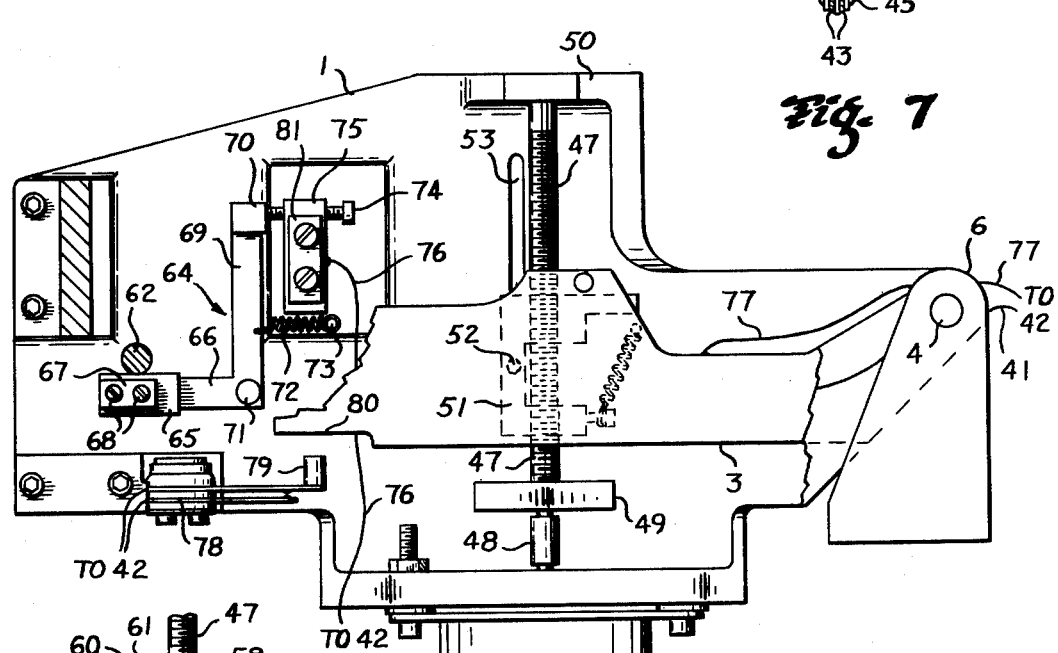
Fig. 5
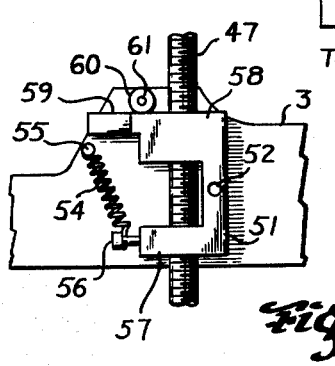
Fig. 6
Fig. 7

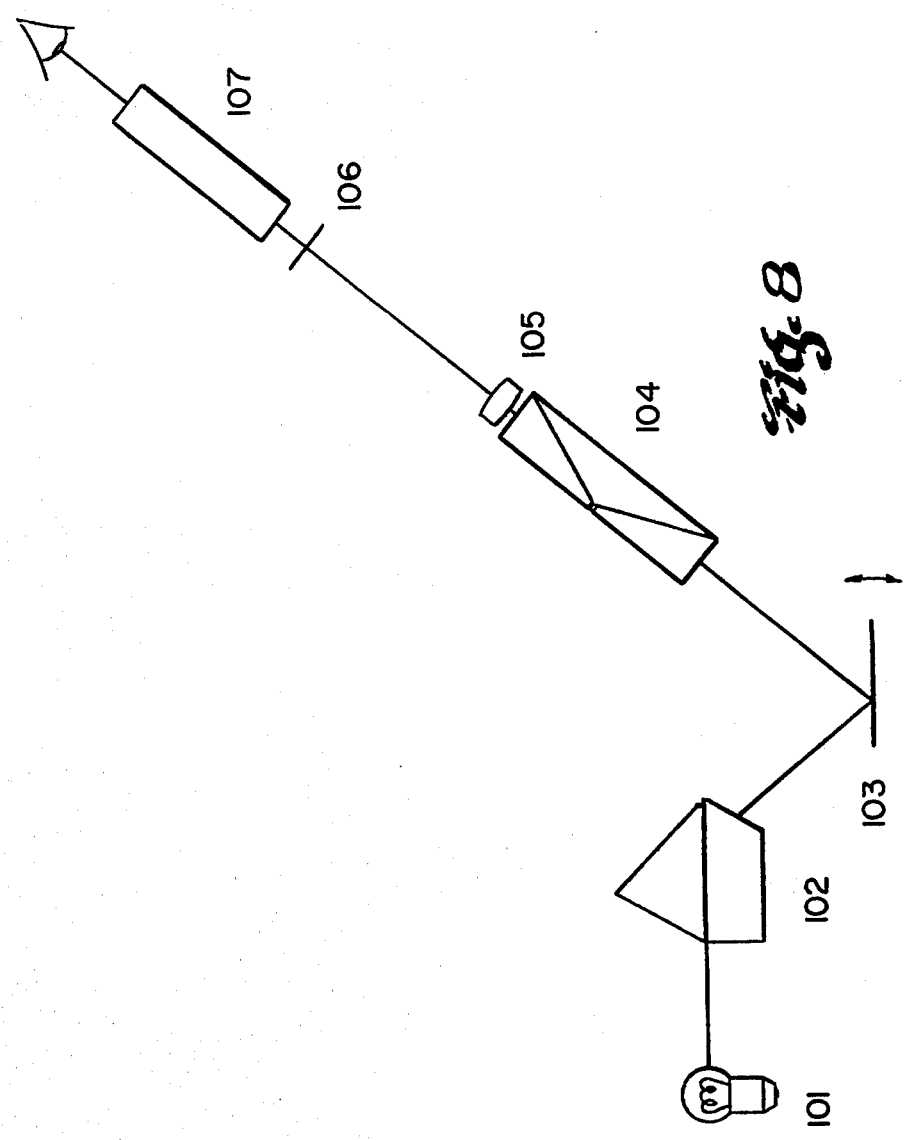

ABBE REFRACTOMETER

BACKGROUND OF THE INVENTION

This invention relates to Abbe refractometers and more particularly to a follower mechanism for determining the mirror position in an Abbe refractometer.

Abbe refractometers are devices for determining the index of refraction of materials with a high degree of accuracy. The measurement is conventionally made by moving a pivotable mirror until a shadow line created by the sample and primary prism is located precisely at the junction of a pair of cross hairs in an eyepiece. The index of refraction is then obtained by reference to a scale and indicator mechanism coupled to the moveable mirror. The optics of such a system are illustrated in copending application Ser. No. 802,741 filed June 2, 1977. The description and drawings of the application are incorporated herein by reference. Referring to FIG. 8, light from illumination source 101 is directed through primary prism 102 having a test sample (not shown) therein to movable mirror 103. Light reflected from the mirror passes through color-compensating prism 104 and is focused by telescope lens 105 on reticle 106 which is observed through eyepiece 107. Sample temperature is a factor which is capable of exerting a substantial influence on the accuracy of the measurement. Therefore, conventional instruments usually of some means of holding the test prism at a constant temperature, frequently, by means of circulating water from a constant temperature bath. These conventional devices have substantial disadvantage in difficulty of maintaining the constant temperature of the bath and accurately monitoring the temperature of the primary prism. In addition, delays result when starting up circulation of the constant temperature fluid and in bringing the constant temperature fluid to a stabilized temperature.

BRIEF DESCRIPTION OF THE PRESENT INVENTION AND DRAWINGS

It is an objective of the present invention to overcome the disadvantages of the such prior art devices.

It is another object of the present invention to provide a follower mechanism capable of accurately determining the position of the movable mirror in an Abbe refractometer.

It is a still further object of the present invention to provide a follower mechanism permitting electronic determination of the index of refraction of a sample tested in an Abbe Refractometer.

It is still another object of the present invention to provide a follower arm—mirror arm combination useful for setting an Abbe refractometer to a reference standard.

The movable mirror of an Abbe refractometer is carried on an arm having a pivot at one end. The mirror is positioned on the arm between the pivot and a contact, which is located at the other end of the arm. The degree of accuracy can be enhanced by positioning the mirror near to the pivot and the contact remote to the mirror. A pivotable follower is mounted to travel in a path parallel to the path of the arm. The follower has a contact cooperating with the contact on the mirror arm to identify the position of the mirror and for conversion of the position to index of refraction. Another set of contacts are used in combination with the first set of contacts to identify the specific location of a standard for calibrating the instrument.

FIG. 1 is a perspective view of the mirror arm and follower assembly of the present invention;

FIG. 2 is a front view, partly in section, of the structure of FIG. 1;

FIG. 3 is a left side view of the mirror arm drive;

FIG. 4 is a right side view, partly in section, showing details of the mirror arm assembly;

FIG. 5 is a right side view, partly in section, having the mirror arm assembly removed to show details of the follower arm assembly;

FIG. 6 is a view of the follower arm drive assembly as seen from the back of FIG. 5 with the frame removed;

FIG. 7 is an end view of the contact carried by the mirror support arm.

FIG. 8 is an illustration of the optics of the system.

DETAILED DESCRIPTION OF A PREFERRED EMBODIMENT

Referring to FIG. 1, a frame 1 carries a mirror support arm 2 and a follower arm 3. Mirror support arm 2 and follower arm 3 are each pivotably mounted by ends 7 and 8, respectively to shaft 4 which extends between ends 5 and 6 of frame 1. The other end 9 of mirror support arm 2 carries an arcuate metal strip 10 displaced from arm 2 by spacers 11 and screws 12 (see FIG. 2). Arcuate metal strip 10 is frictionally engaged between disks 13 and 14. Washer 15 and screw 16 hold disks 13 and 14 against the end of shaft 17. FIG. 3 shows an enlarged view of the relationship of disks 13 and 14 to arcuate strip 10. Referring again to FIG. 1, shaft support 18 is secured to frame 1 by bolts 19 and 20. Course adjustment knob 21 is coupled directly to shaft 17, which passes through support 18, and fine adjustment knob 22 is indirectly coupled by conventional reduction means (not shown) to shaft 17. As one of these knobs is rotated, shaft 17 rotates disks 13 and 14. Disks 13 and 14 frictionally engage arcuate strip 10 to transfer the rotational motion of shaft 17 into the arcuate motion of mirror support arm 2. Mirror 23 is cemented to mirror mount 24 which is held against edge 25 of arm 2 by springs 26 (one shown) extending between pins 27 protruding from mirror mount 24 and pins 28 (one shown) on arm 2. Precise mirror positioning on mirror support arm 2 is accomplished by adjustment screws 29 and 30.

FIG. 4 shows additional construction details of mirror support arm 2. First "L-shaped" member 31 is pivotably mounted to mirror support arm 2 by pivot 32. Spring 33 extends between screw 34 on mirror support arm 2 and first "L-shaped" member 31 to bias leg 35 against set screw 36. Set screw 36 passes through block 37 threadably engaging a bore therein. Block 37 is mounted to mirror support arm 2 by screws 38. Leg 39 of first "L-shaped" member 31 has a contact 40 mounted thereto and insulated therefrom. Electric lead 41 connects contact 40 with control 42 (see FIG. 2). FIG. 7 shows the assembly of the contact 40 to leg. 39. Insulators 43 are positioned on either side of contact 40 and retain contact 40 by pressure applied between plate 44 and leg 39 through screws 45.

Referring to FIG. 5, the structural details, drive mechanism and contact assembly for follower arm 3 are shown in greater detail. Stepping motor 46 is connected to lead screw 47 by coupling 48. Protrusions 49 and 50 extending from frame 1, support lead screw 47 for rotational movement. Follower 51 threadably engages lead-screw shaft 47 and has pin 52 extending therefrom which slideably engages vertical slot 53 in frame 1, to prevent follower 51 from rotating with lead screw 47.

Referring to FIG. 6, spring 54 extends between pin 55 on follower arm 3 and screw 56 extending out of the lower portion 57 of follower 51. Upper portion 58 of follower 51 has a flat surface 59 on which bearing 60 rides. Bearing 60 is mounted to follower arm 3 by shaft 61 and is held in contact with flat surface 59 by bias applied by spring 54. Pin 62 (FIG. 5) extends through end 63 (FIG. 4) of follower arm 3. Second "L-shaped" member 64 (FIG. 5) has an uninsulated contact 65 fastened to leg 66 by plate 67 and screws 68. Leg 69 has a contact 70 and the entire L member is pivotable about pivot pin 71. Spring 72 extends between leg 69 and screw 73 mounted on frame 1 to bias contact 70 against screw 74 threadably mounted through block 75. Block 75 is insulated from frame 1 by nonconductive plates 81 to provide electrical isolation and block 75 is connected through lead 76 to control 42. Lead 77 connects follower arm 3 to control 42. Switch 78 has normally open contacts and bumper 79 is adapted to be engaged by edge 80 of follower arm 3 when follower arm 3 reaches a predetermined position to close switch 78.

In operation, mirror support arm 2 is moved to a predetermined position by an operator. Upon actuation of control 42 stepping motor 46 rotates shaft 47 driving follower 51 and follower arm 3 upwards until pin 62 (FIG. 4) touches contact 40. Control 42 counts the number of steps through which motor 46 has progressed to determine the position of mirror 23.

The relative positions of mirror support arm 2 and follower arm 3 illustrated in FIG. 4 demonstrate the location of a "standard" position. Such a standard position is desirable for calibration purposes. This "standard" location is determined by a position of follower arm 3 (FIG. 5) and mirror support arm 2 such that contact is simultaneously made between pin 62/contact 40 and between contact 70/screw 74. In an Abbe refractometer a mirror position suitable for such a "standard" location is a position representing the index of refraction of distilled water @ 20° C. Adjustment of screws 36 and 74 permit precise independent positioning of both mirror support arm 2 and follower arm 3. Usually control 42 is adapted to immediately return follower arm 3 to a normal reset position as determined by closing of switch 78.

In an Abbe refractometer, the determination of the index of refraction is accomplished by measuring the relative angle of refraction produced when light passes through a sample. One such means of measuring the angle of refraction is by tilting a mirror. The relative angle of the mirror is readily convertible to index of refraction. The apparatus described above provides a convenient form for determining the angle of the mirror, since the number of steps of the stepping motor required to drive the follower from the "standard" reference position to the "corresponding" position is easily translatable to mirror angle or, preferably, index of refraction.

What is claimed is:

1. In a refractometer having a frame, a primary prism for holding a specimen, a light source, and a movable mirror, the improvement comprising mounting means carrying said mirror and connected to said frame for movement along a first path, first drive means for moving said mounting means to a selected position, follower means connected to said frame for movement along a second path, a rest position for the follower being located at one end of said second path, electric means for driving said follower along the second path, said electric means being responsive to a signal, control means for generating said signal, means for activating said control means, said control means being responsive to said follower reaching a location along the second path corresponding to the selected position of said mounting means on the first path, whereby upon activation of the control means, the electric means drives the follower from the rest position to an equivalent position corresponding to the selected position of said mounting means and then back to said rest position.

2. The improvement of claim 1 wherein said mounting means and follower means are pivotably connected to said frame for arcuate movement about a common axis.

3. The improvement of claim 2 wherein said electric means includes a stepping motor, a lead screw connected to said motor, a threaded follower engaging the threads of said lead screw and having a flat surface normal to the axis of said lead screw and extending parallel to said follower means, a bearing mounted on said follower means by the inner race, said bearing having an outer race engaging said flat surface and means to bias the outer race of said bearing against said flat surface.

4. The improvement of claim 1 wherein said electric means includes a stepping motor, a lead screw connected to said motor for rotation therewith and a member connected to said follower means and engaging said lead screw to move said follower means in response to rotation of said shaft.

5. The improvement of claim 1 wherein said mounting means carries a first contact, said follower means carries a second contact and said first and second contacts touch upon arrival of said follower means at the equivalent position.

6. The improvement of claim 1 wherein a first electrical contact is carried by said mounting means, second electrical contact is carried by said follower means, said first and second electrical contacts comprise a first switch, a second switch mounted on said frame, said second switch having normally open contacts adapted to be closed by said follower means upon arrival of said follower means at a chosen location to provide a calibration position indicated by the simultaneous closing of said first and second switches.

7. The improvement of claim 6 wherein said first electrical contact is carried by one leg of an L shaped member, the L shaped member being pivotably mounted at its apex for movement parallel to said first path, the other leg of the L shaped member being biased against a first adjustment means, said second contact being a rod extending through said follower means normal to said second path and one end of said rod intersecting said first path.

8. The improvement of claim 1 wherein said drive means comprises a shaft rotatably mounted in and extending through said frame, one end of said shaft having means for manual rotation, a pair of flat flexible disks centrally secured to the other end of said shaft for rotation therewith, a flat driven member mounted to said mounting means and having an edge passing between said pair of disks, whereby friction between said driven member and disks moves said mounting means when said shaft is rotated.

9. The improvement of claim 8 wherein said first path is arcuate and has a radius substantially larger than the radius of said disks.

* * * * *